US011464463B2

(12) United States Patent
Sun et al.

(10) Patent No.: US 11,464,463 B2
(45) Date of Patent: Oct. 11, 2022

(54) ELASTOGRAPHY BASED ON X-RAY COMPUTED TOMOGRAPHY AND SOUND WAVE INTEGRATION

(71) Applicant: The Regents of the University of California, Oakland, CA (US)

(72) Inventors: Lizhi Sun, Irvine, CA (US); Dongxu Liu, Irvine, CA (US); Zhijian Hu, Irvine, CA (US); Ge Wang, Troy, NY (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 663 days.

(21) Appl. No.: 16/384,068

(22) Filed: Apr. 15, 2019

(65) Prior Publication Data

US 2019/0313984 A1 Oct. 17, 2019

Related U.S. Application Data

(60) Provisional application No. 62/657,392, filed on Apr. 13, 2018.

(51) Int. Cl.
*A61B 6/00* (2006.01)
*A61B 8/08* (2006.01)
(Continued)

(52) U.S. Cl.
CPC ............ *A61B 6/032* (2013.01); *A61B 6/5217* (2013.01); *A61B 6/5235* (2013.01);
(Continued)

(58) Field of Classification Search
CPC ........ A61B 6/032; A61B 6/508; A61B 6/5247
See application file for complete search history.

(56) References Cited

U.S. PATENT DOCUMENTS

2004/0234113 A1* 11/2004 Miga .................... G06T 7/0012
382/128
2007/0189449 A1* 8/2007 Baumann ............... A61B 6/482
378/44
(Continued)

FOREIGN PATENT DOCUMENTS

DE 102009018882 A1 * 10/2010 ........... A61B 5/0053

OTHER PUBLICATIONS (Mar. 2018). Wavelet synchrosqueezing. MathWorks. https://www.mathworks.com/help/releases/R2018a/wavelet/gs/wavelet-synchrosqueezing.html (Year: 2018).*

(Continued)

*Primary Examiner* — Carolyn A Pehlke
*Assistant Examiner* — Johnathan Maynard
(74) *Attorney, Agent, or Firm* — Nguyen Tarbet LLC

(57) ABSTRACT

Systems and methods for integrating a three-dimensional X-ray computed tomography system with an independent sound wave system to determine mechanical properties of tissue using signals from the sound wave system. Methods are disclosed that generate a numerical simulation and take the transmitted wave signals as the optimization objective to estimate modulus distribution of the tissue. Further, the mechanical properties of the tissue are reconstructed based on an inverse algorithm.

20 Claims, 13 Drawing Sheets
(9 of 13 Drawing Sheet(s) Filed in Color)

(51) Int. Cl.
*A61B 6/03* (2006.01)
*G06T 7/00* (2017.01)
(52) U.S. Cl.
CPC ............ *A61B 6/5247* (2013.01); *A61B 8/485* (2013.01); *G06T 7/0016* (2013.01); *G06T 2207/10081* (2013.01)

(56) References Cited

U.S. PATENT DOCUMENTS

| | | | | |
|---|---|---|---|---|
| 2007/0238966 | A1* | 10/2007 | Sun | A61B 5/442 600/407 |
| 2011/0319756 | A1* | 12/2011 | Zheng | G01S 7/52022 600/438 |
| 2013/0218002 | A1* | 8/2013 | Kiraly | A61B 5/0051 600/411 |
| 2017/0238884 | A1* | 8/2017 | Jeong | G16H 50/30 |

OTHER PUBLICATIONS

Catheline, S., Benech, N., Brum, J., & Negreira, C. (2008). Time reversal of elastic waves in soft solids. Physical review letters, 100(6), 064301. (Year: 2008).*

Parker, K. J., Ormachea, J., Zvietcovich, F., & Castaneda, B. (2017). Reverberant shear wave fields and estimation of tissue properties. Physics in Medicine & Biology, 62(3), 1046. (Year: 2017).*

Brum, J., Catheline, S., Benech, N., & Negreira, C. (2015). Quantitative shear elasticity imaging from a complex elastic wavefield in soft solids with application to passive elastography. IEEE transactions on ultrasonics, ferroelectrics, and frequency control, 62(4), 673-685. (Year: 2015).*

Liu, Y., Wang, G., & Sun, L. Z. (Jan. 2004). Principle and Algorithm for Tomography-Based 3-D Anisotropic Elastography. In ASME International Mechanical Engineering Congress and Exposition (vol. 47039, pp. 315-316). (Year: 2004).*

Liu, Y., Wang, G., & Sun, L. Z. (2006). Anisotropic elastography for local passive properties and active contractility of myocardium from dynamic heart imaging sequence. International Journal of Biomedical Imaging, 2006. (Year: 2006).*

(Mar. 2018). Time-Frequency reassignment and mode extraction with synchrosqueezing. MathWorks. https://www.mathworks.com/help/releases/R2018a/wavelet/examples/time-frequency-reassignment-and-mode-extraction-with-synchrosqueezing.html (Year: 2018).*

Wang, Z. G., Liu, Y., Sun, L. Z., Wang, G., & Fajardo, L. L. (2006). Elasto-mammography: theory, algorithm, and phantom study. International journal of biomedical imaging, 2006. (Year: 2006).*

Wang, Z. G., Liu, Y., Wang, G., & Sun, L. Z. (2009). Elastography method for reconstruction of nonlinear breast tissue properties. International Journal of Biomedical Imaging, 2009. (Year: 2009).*

Op den Buijs, J., Hansen, H. H., Lopata, R. G., de Korte, C. L., & Misra, S. (2011). Predicting target displacements using ultrasound elastography and finite element modeling. IEEE Transactions on Biomedical Engineering, 58(11), 3143-3155. (Year: 2011).*

Assaad, W., & Misra, S. (2013). Combining ultrasound-based elasticity estimation and FE models to predict 3D target displacement. Medical engineering & physics, 35(4), 549-554. (Year: 2013).*

Prince, J. L., & Links, J. M. (2006). Medical imaging signals and systems. "Chapter 5: Projection Radiography." Upper Saddle River: Pearson Prentice Hall. (Year: 2006).*

* cited by examiner

ELASTOGRAPHY BASED ON X-RAY COMPUTED TOMOGRAPHY AND SOUND WAVE INTEGRATION

CROSS-REFERENCES TO RELATED APPLICATIONS

This application is a non-provisional and claims benefit of U.S. Provisional Application No. 62/657,392, filed Apr. 13, 2018, the specification(s) of which is/are incorporated herein in their entirety by reference.

GOVERNMENT SUPPORT

This invention was made with government support under Grant No. CMMI-1229405 awarded by the National Science Foundation. The government has certain rights in the invention.

BACKGROUND OF THE INVENTION

Field of the Invention

The present invention relates to medical imaging and materials characterization, in particular, to elastography based on X-ray computed tomography (CT) and sound wave integration.

Background Art

Elastography framework relies on external excitations or perturbations, such as mechanical waves, which generate mechanical responses such as wave velocity, wavelength, and/or displacement measurable deep inside a tissue to map the distribution of elastic moduli within a region of interest of the tissue. However, direct measurements based on images suffer from issues such as image noise and low spatial resolution because of tissue interfaces. These problems restrict detectable tissue categories and clinical application. Previous elastography based on computed tomography (CT) alone requires two CT scans, which exposes the sample to higher amounts of radiation. Ultrasound implements high frequencies which only carry little mechanical energy and do not long distances because of high attenuation, therefore a mechanical response in unobtainable from the sample.

To resolve these problems, the present invention discloses an elastography method based on integration of X-ray computed tomography (CT) imaging and sound wave testing methods to characterize mechanical properties of tissues, without relying on the direct measurement of internal responses such as the wave velocity, wavelength, and/or displacement within the tissues. The present invention may be additionally used to characterize mechanical properties of engineering materials.

BRIEF SUMMARY OF THE INVENTION

An integrated elastography method is disclosed that combines three-dimensional X-ray tomography and independent sound wave test. To put the combination into numerical simulation and take the transmitted wave signals as the optimization objective, the modulus distribution is reconstructed based on the inverse algorithm. For implementing this invention, the 3D image model is obtained from an X-ray CT modality, and the excitation and the response are pulsed and collected by sound transducers around the object, respectively. Some of transducers are sound sources, while others are receivers which are used to measure the transmitted signals. The collected data can be displacement, velocity, acceleration or pressure on the object surface.

In some aspects, the present invention discloses an integrated elastography system for estimating mechanical properties of a sample, the system comprising an x-ray computed tomography ("CT") system comprising an x-ray source and a detector, wherein the x-ray source emits x-rays towards the sample and wherein the detector collects x-rays emitted from the sample. The system additionally comprises a sound wave system having one or more acoustic transducers and one or more receivers positioned around the outer surface of the sample, wherein the one or more transducers are configured to generate sound waves that impinge on the sample, and wherein the one or more receivers receive a first set of transmitted signals, wherein the first set of transmitted signals include the sound waves that transmit through the sample.

The system additionally includes a controller operably coupled to the x-ray CT system and the sound wave system, wherein the controller has memory that stores computer readable instructions that, when executed by the controller, causes the controller to generate an x-ray CT image of the sample, using the x-ray CT system, and select a matrix and an inclusion based on geometries detected from the CT image of the sample. The controller may additionally generate the first set of transmitted signals based on the CT image using the sound wave system, select an initial set of values comprising one or more of an elasticity modulus, a Poisson ratio, and a density for the matrix and the inclusion based on the selection, and perform and repeat a forward analysis sequence to simulate a sound wave transmission through the matrix and the inclusion to deduce a mechanical response of the matrix and the inclusion. The forward analysis sequence may include optimizing the initial set of values until the set of signals generated converges with the first set of transmitted signals and the mechanical response may be deduced based on the set of signals, thereby decoding the mechanical response without relying on the response acquisition within the sample.

In some embodiments, the forward analysis sequence may include constructing a finite element ("FE") model by generating a mesh of each of the matrix and of the inclusion from the CT image, wherein the mesh is generated using an approximation of the geometries of the matrix and the inclusion, and wherein generation of the mesh includes dividing the CT image into smaller finite elements. In some embodiments, the memory may include additional instructions that, when executed by the controller, cause the controller to perform an inverse analysis on the set of signals to deduce a modulus of each of the matrix and the inclusion. The inverse analysis may include a wavelet synchrosqueezed transform ("WSST").

In some embodiments, the WSST may include generating a continuous wavelet transform from the set of signals, extracting instantaneous frequency from the continuous wavelet transform, reconstructing transmitted signals from continuous wavelet transform and the frequency, and decoding the reconstructed transmitted signals into shear signals and pressure signals, and estimating the modulus of the sample based on one or more of the shear signals and the pressure signals, thereby decoding the mechanical property of the sample using the x-ray CT image and the transmitted signals.

In some embodiments, the estimation may be based on a time reversal theory, wherein the modulus may be estimated from the shear signals and the pressure signals. The one or more transducers may be disposed on a surface of an enclosure of the integrated elastography system and wherein the plurality of receivers may be in contact with the sample. In some embodiments, the sound waves may be harmonic waves, sinusoidal tone burst, square waves, triangle waves and so on in the wide frequency range, such as from 100 Hz to 100 kHz. The initial set of values may be selected based on a reasonable and educated estimate of the elasticity modulus, the Poisson ratio, and the density for the matrix and the inclusion. The mechanical response may include one or more of displacement, velocity, acceleration, and a pressure within the sample.

In some embodiments, the sample may be a biological sample and the matrix may include tissue and the inclusion may include non-tissue biological material. In some embodiments, the biological material may be a tumor or mass. In some embodiments, the sample may include particles embedded in a solidified medium.

According to some embodiments, an integrated elastography system is provided. The system may include an x-ray computed tomography ("CT") system comprising an x-ray source and a detector wherein the x-ray source emits x-rays towards a sample and wherein the detector collects x-rays emitted from the sample. The system may additionally include a sound wave system having a plurality of acoustic transducers and a plurality of receivers positioned around the outer surface of the sample. The plurality of transducers is configured to generate sound waves that impinge on the sample, and the plurality of receivers receives a first set of transmitted signals. The first set of transmitted signals includes the sound waves that transmit through the sample.

The system may additionally include a controller operably coupled to the x-ray CT system and the sound wave system. The controller can have a memory that stores computer readable instructions that, when executed by the controller, causes the controller to perform operations. These operations may comprise: (i) generate an x-ray CT image of the sample and select a matrix and an inclusion based on geometries detected from the CT image of the sample, (ii) generate a mesh of each of the matrix and of the inclusion, wherein the mesh is generated using an approximation of the geometries of the matrix and the inclusion, wherein the mesh is generated from the CT image, and wherein generation of the mesh includes dividing the CT image into smaller finite elements, (iii) choose an initial set of values comprising one or more of an elasticity modulus, a Poisson ratio, and a density for the matrix and the inclusion based on the selection, (iv) perform a finite element analysis on the CT image using the set of initial values of an elasticity modulus, a Poisson ratio, and a density of the sample to generate a second set of transmitted signals, (v) perform a wavelet synchro-squeezed transform ("WSST") of a deformation of shear and pressure waves outputted from finite element analysis to generate a continuous wavelet transform, (vi) extract instantaneous frequency from the continuous wavelet transform, (vii) reconstruct the transmitted signals from continuous wavelet transform and the frequency, and (viii) decode the reconstructed transmitted signals into shear signals and pressure signals. The controller may repeat step (iv)-(viii) to optimize the set of initial values and generate the second set of transmitted signals until the second set of transmitted signals converge with the first set of transmitted signals, and (ix) estimate an elastic modulus of the sample based on one or more of the shear signals and the pressure signals, wherein the estimation is based on a time reversal theory, and wherein a mechanical property of the sample is estimated from the elastic modulus, thereby decoding the mechanical property of the sample using the x-ray CT image and the transmitted signals without relying on the response acquisition within the sample.

In some embodiments, the time reversal theory may include generating a time reversal displacement field and a time reversal strain field, wherein the elastic modulus is determined from a ratio of the time reversal displacement field and the time reversal strain field. In some embodiments, the sound waves may include a sine tone burst and the initial set of values may be chosen based on a reasonable and educated estimate of the elasticity modulus, the Poisson ratio, and the density for the matrix and the inclusion. The time reversal analysis may include a WSST.

According to some embodiments, a method for determining a modulus of a sample is provided. The method may comprise obtaining an x-ray CT image of the sample using x-rays collected from the sample. The x-rays are collected using an x-ray CT system comprising an x-ray source that emits x-rays towards the sample and a detector that collects x-rays emitted from the sample. The method continues with positioning at or near an outer surface of the sample a sound wave system comprising one or more acoustic transducers and one or more receivers. The one or more transducers can generate sound waves such as, for example, a sine tone burst, and the one or more receivers receive a first set of transmitted signals. The method may additionally include impinging the sample with the sound waves generated from the one or more transducers. The one or more receivers then receive the first set of transmitted signals, which include the sound waves that transmit through the sample. The method may additionally perform a finite element analysis on the CT image using a set of initial values of an elasticity modulus, a Poisson ratio, and a density of the sample to generate a second set of transmitted signals, and perform a cycle operation of optimizing the set of initial values and generating the second set of signals until the second set of signals converge with the first set of transmitted signals; and determining mechanical response of the sample based on the optimized set of initial values, wherein the mechanical response includes one or more of a displacement, a velocity, an acceleration, and a pressure of the sample.

In some embodiments, the method may further include performing an inverse analysis on the second set of signals to deduce a modulus of the sample. The inverse analysis may include a wavelet synchro-squeezed transform ("WSST"). The WSST may include generating a continuous wavelet transform from the set of signals, extracting instantaneous frequency from the continuous wavelet transform, reconstructing transmitted signals from continuous wavelet transform and the frequency; decoding the reconstructed transmitted signals into shear signals and pressure signals; and estimate the elastic modulus of the sample based on one or more of the shear signals and the pressure signals, wherein the estimation is based on a time reversal theory, and wherein the elastic modulus is estimated from the shear signals and the pressure signals, thereby decoding mechanical property of the sample using the x-ray CT image and the transmitted signals.

In some embodiments, performing the finite element analysis on the CT image may include selecting a matrix and an inclusion based on geometries detected from the CT image of the sample; and generating a mesh of each of the matrix and of the inclusion, wherein the mesh is generated using an approximation of the geometries of the matrix and the inclusion, wherein the mesh is generated from the CT image, and wherein generation of the mesh includes dividing the CT image into smaller finite elements. The method may further include determining the mechanical response and the modulus of each of the matrix and the inclusion.

One of the unique and inventive technical features of the present invention is the transmission of sound signals entering from the outside of the sample. Without wishing to limit the invention to any theory or mechanism, it is believed that the technical feature of the present invention advantageously provides for a method to determine the mechanical parameters, such as pressure, velocity, displacement, strain or wavelength, from the outside of the sample and obtain the physical properties of the sample from the parameters. This eliminates that need to use complex and/or invasive imaging techniques to acquire mechanical parameters inside the sample. None of the presently known prior references or work has the unique inventive technical feature of the present invention.

Moreover, waves in solid have mode conversion and scattering at interfaces, which introduces challenges in modeling and inverse convergence. Traditionally, in order to inversely have a converging and reliable analysis, internal measurement of mechanical responses is necessary. Thus, one of ordinary skill in the art would perceive that the combination of using x-ray CT imaging with acoustic sound would not work because information from the outside of the sample would be insufficient. Contrary to current belief, the inventive technical feature of using x-ray CT imaging with acoustic sound at the outside of the sample was surprisingly found to work in determining the mechanical properties of the sample. This provided an additional benefit of eliminating the need for multiple CT scans, thus only one x-ray CT image of the sample was required to perform elastography.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which.

DESCRIPTION OF PREFERRED EMBODIMENTS

Figure 1A:
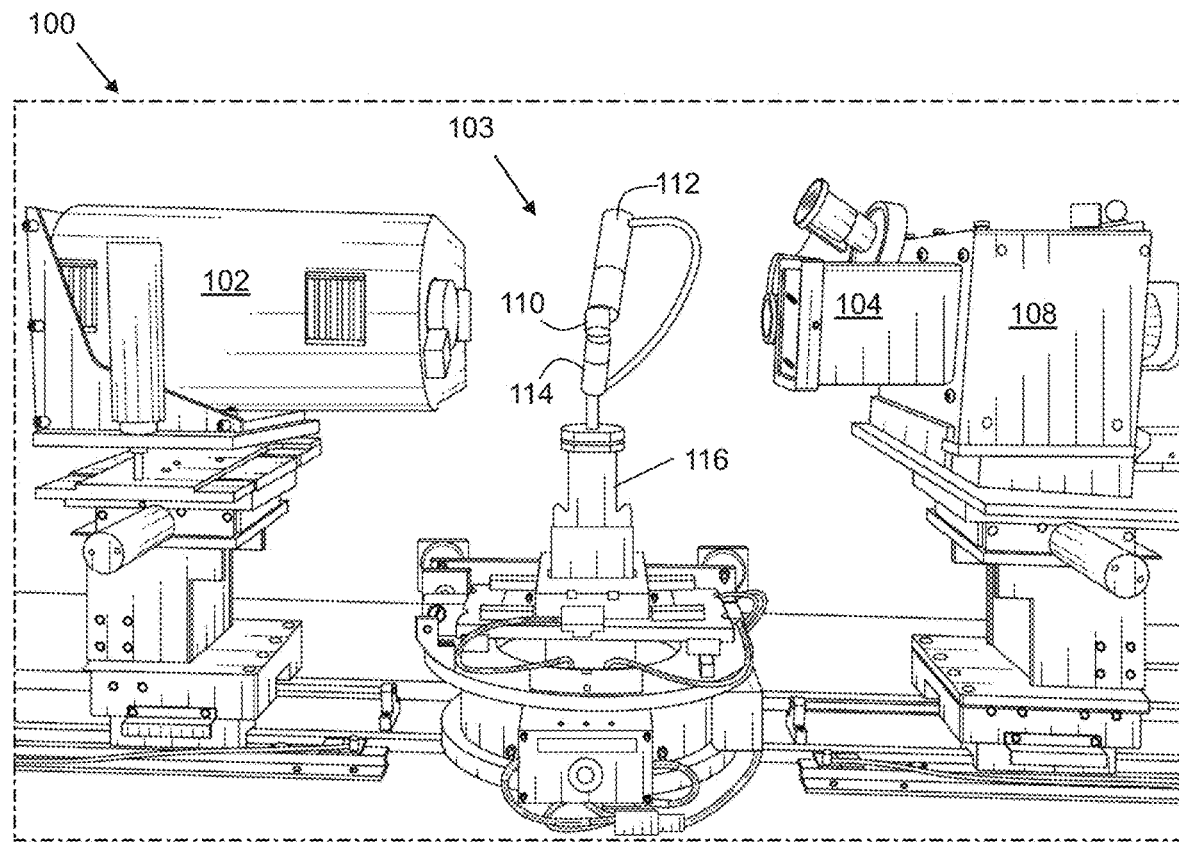
FIG. 1A shows a non-limiting embodiment of an integrated elastography system of the present invention.

Following is a list of elements corresponding to a particular element referred to herein:

| | |
|---|---|
| 100 | integrated elastography system |
| 101 | x-ray CT imaging system |
| 102 | x-ray source |
| 103 | sound wave system |
| 104 | objective |
| 108 | detector |
| 110 | sample |
| 112 | transducer |
| 114 | receiver |
| 120 | controller |
| 202 | incident waves |
| 204 | object |

As used herein, the term "matrix" corresponds to a substrate, which may be of a continuous material. An "inclusion" refers to a material(s), i.e. object, embedded in the matrix. For instance, in biological applications, the matrix may include a tissue and the inclusion may be a tumor. Matrix and inclusion represent different tissues/materials. The matrix is the continuous material into which the inclusion(s) is/are embedded, whereas the inclusion is the material embedded into the matrix. In engineering, particle-filled composites are examples of matrix/inclusion systems.

As used herein, the term "mesh" refers to a representation of finite element. The mesh is generated by dividing the matrix and inclusion into smaller finite elements.

Referring now to FIGS. 1-18B, the present invention features an integrated elastography method that combines 3D X-ray CT and independent sound wave testing methodologies. More specifically, the present invention includes performing numerical simulation using transmitted sound wave signals as the optimization objective and reconstructing a modulus distribution based on an inverse algorithm. A non-limiting embodiment of the integrated elastography system (100) of the present invention is shown in FIG. 1.

In one embodiment, the integrated elastography system (100) may include a 3D x-ray CT imaging system (101) having an x-ray source (102) and a detector (108). A sample (110) may be positioned in the integrated elastography system (100) such that x-rays emitting from the source (102) impinge on the sample, and the transmitted x-rays may be focused by an objective (104) onto the detector (108). A controller (120) of the integrated elastography system (100) may generate a 3D image of the sample from the signals received by the detector (108). The integrated elastography system (100) may additionally include a sound wave system (103) having a plurality of transducers positioned around the sample for exciting the sample and a plurality of receivers positioned around the sample for receiving the response of the sample due to the excitation. As an example, the plurality of transducers may include acoustic or sound transducers (112) configured to generate sound waves, and additionally include acoustic receivers (114) configured to receive signals transmitted through the sample.

Figure 1B:
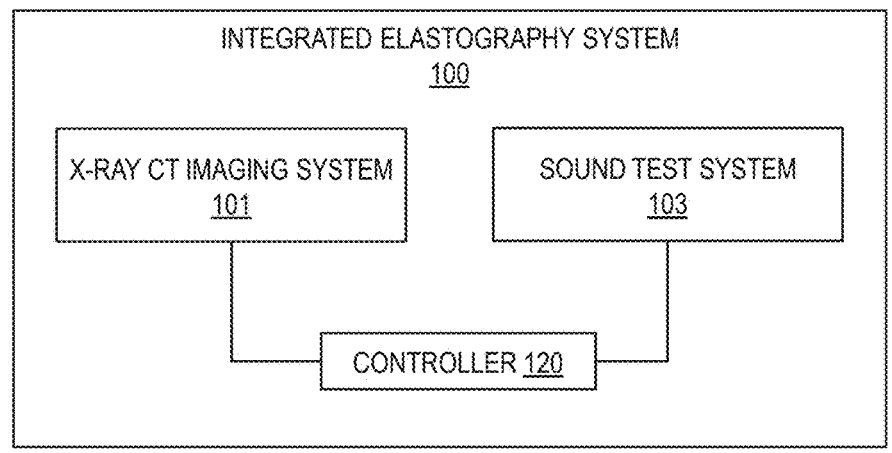
FIG. 1B shows a schematic diagram of the integrated elastography system having a controller and an X-ray computed tomography (CT) integrated with a sound wave system.
Figure 3:
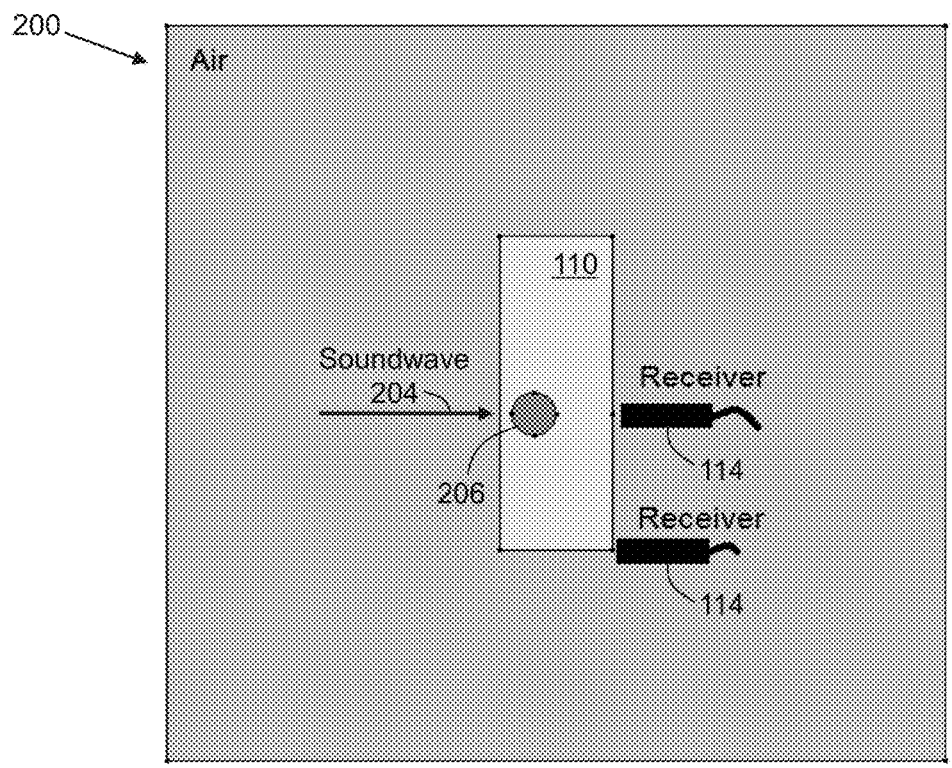
FIG. 3 shows a schematic illustration of sound waves incident on a sample positioned within the integrated elastography system, and transmitted signals collected using receivers of the integrated elastography system.

For illustrative purposes, only one acoustic transducer and one acoustic receiver is shown in FIG. 1A. However, it is to be understood that the number of transducers and receivers should be enough for exciting each phase and receiving the transmission and reflection through each phase, for acquiring the mechanical responses outside the sample without internal measurement. In some embodiments, the number of transducers may be 1-5 or greater than 5. In other embodiments, the number of receivers may be 1-5 or greater than 5. In yet other embodiments, the number of receivers may be greater than the number of transducers. For instance, a transducer may emit the sound waves, and multiple receivers may be positioned around the sample to collect the signals transmitting though the sample as shown in FIG. 3.

In non-limiting examples, a plurality of acoustic transducers and a plurality of receivers may be positioned around the outer surface of the sample. In some embodiments, an acoustic transducer, such as a pulser, may be assembled on a frame attached to a roof of an enclosure of the integrated elastography system (100) and a receiver may be positioned such that the receiver is in contact or touches the outer surface of the sample (110). Herein, incident waves (204) may be emitted from the acoustic transducer (112), and the sound waves (204) may pass through the sample (110) and an object (206) within the sample (110). Signals transmitted from both the sample and the object may be collected by multiple receivers (114) positioned around the sample (110), for example, near or at the sample's surface. The controller (120) may use the transmitted signals collected from the acoustic receivers (114) to generate information such as displacement, velocity, acceleration or pressure on the sample surface, for example. The controller (120) of the integrated elastography system (100) may control one or more of the components of the x-ray CT imaging system (101) and the sound wave system (103).

Figure 2:
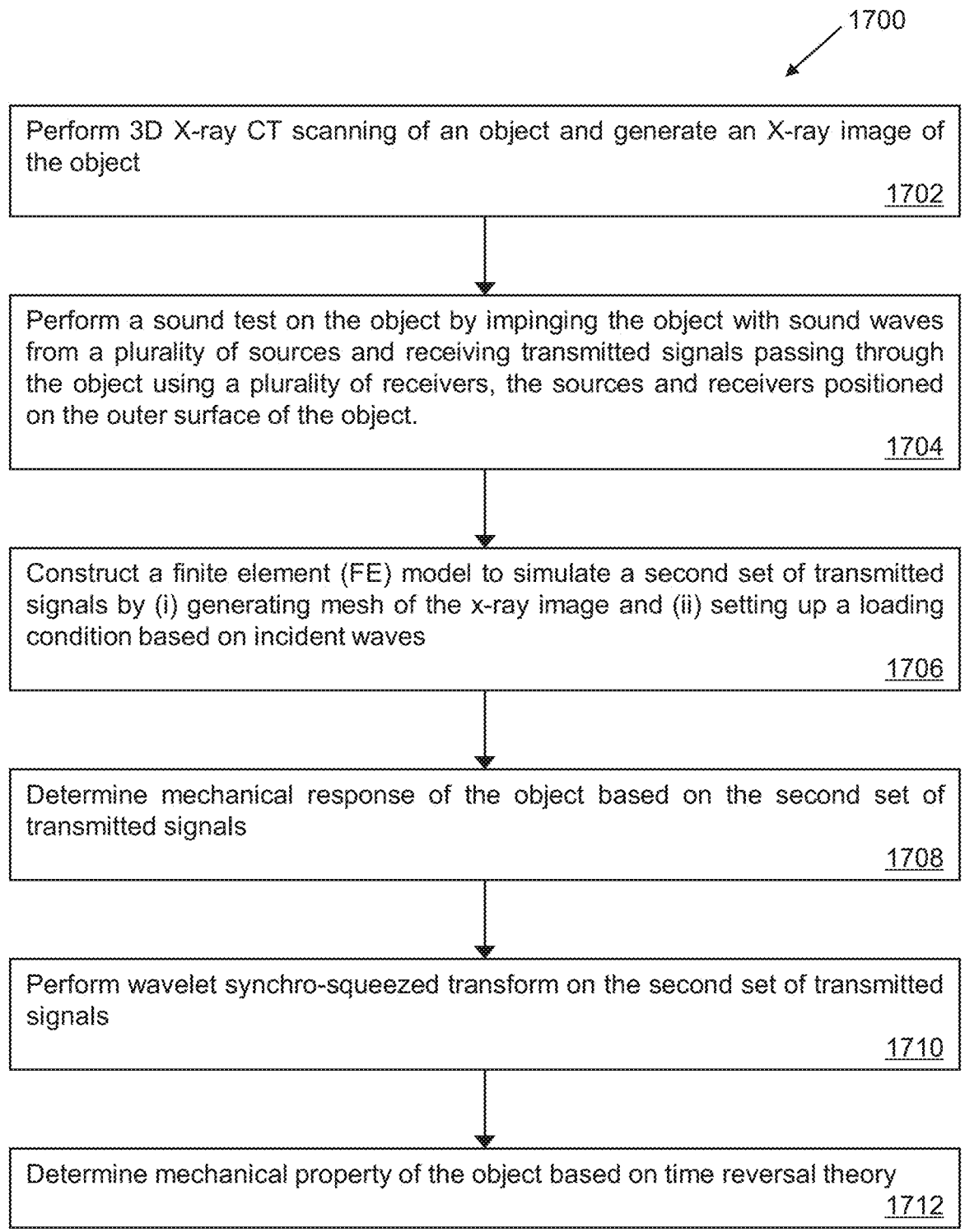
FIG. 2 is a flow chart depicting an example elastography method that integrates X-ray CT imaging and sound wave testing.

According to another embodiment, the present invention discloses an elastography method (1700) that integrates X-ray CT and sound wave testing to estimate the mechanical properties from transmitted sound signals, without using any complex image processing techniques. Turning now to FIG. 2, at 1702 of method 1700, a 3D x-ray CT scanning of an object/sample/tissue positioned within an integrated elastography system (such as the integrated elastography system (100) of FIG. 1A) is performed. Using an x-ray source of the integrated elastography system, an x-ray CT image of the objects is generated. At 1704, method 1700 includes performing a sound test on the object wherein the sound test includes exciting the object with an incident wave emitted from a plurality of sources and receiving a first set of transmitted signals passing through the object using a plurality of receivers. Preferably, the plurality of sources and the plurality of receivers are positioned at or near an outer surface of the sample (110).

In some embodiments, the present invention utilizes two procedures: a forward analysis (e.g. a finite element analysis (performed at 1706 and 1708)) to estimate a mechanical response of the object, and an inverse analysis (e.g., a wavelet synchro-squeezed transform (WSST) (performed at 1710 and 1712)) to estimate a mechanical property of the object, as explained below.

For the forward analysis procedure, the method proceeds to step 1706. In one embodiment, the method includes constructing an FE model to simulate a second set of transmitted signals by generating a mesh of the x-ray CT image (obtained at 1702) and further setting up a loading condition based on incident waves. As an example, the mesh may be generated based on the CT image and the wavelength. The mesh type may be same for both the matrix and the inclusion. The loading condition may be the external excitation in FE simulation and set and copied as the incident wave at 1706.

The FE model may be continuously generated by changing an initial set of values so that the second set of transmitted signals converges with the first set of transmitted signals, for example. Herein, the initial set of values includes one or more of an elasticity modulus, a Poisson ratio, and a density for the matrix and the inclusion based on the selection. As such, steps 1706 and 1708 form a calculating cycle in which 1708 provides guessing a set of values for 1706. The cycle comes to end when the FE simulation meets the measurements. To summarize, with an educated guess of the initial set of values of matrix and inclusion, the FE simulation starts. FE output (or the second set of transmitted signals) is determined based on the initial set of values. At each iteration of the FE model, the set of values such as the elasticity modulus, the Poisson ratio, and the density for the matrix and the inclusion are changed and the output of the FE model is generated using the new set of values. After the iteration is completed, its output is compared with the real measurement (e.g., first set of signals). If the FE output matches with the real measurement, the FE simulation stops. Otherwise, FE simulation continues with newly estimated mechanical parameters of the matrix and inclusion. The FE model is explained in detailed below, using numerical simulation.

SIMULATION EXAMPLE 1

The following is a non-limiting example of a numerical simulation. It is to be understood that the example described herein is presented for illustrative purposes, and is not intended to limit the invention in any way. Equivalents or substitutes are within the scope of the invention.

Numerical Simulation

The finite element analysis (FEA) is a numerical method for solving problems of engineering and mathematical physics. FEA formulation of the problem results in a system of algebraic equations. The method yields approximate values of the unknowns at discrete number of points over the domain. To solve the problem, a large problem is subdivided into smaller parts that are called finite elements. The equations that model these finite elements are then assembled into a larger system of equations that models the entire problem. FEM then uses variational methods from the calculus of variations to approximate a solution by minimizing an associated error function.

Figure 4A:
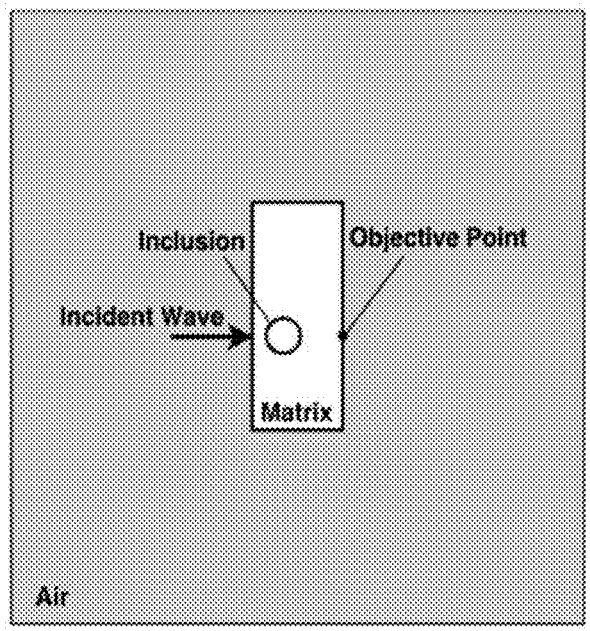
FIG. 4A shows a schematic of a two-dimensional (2D) model and a cross-section of a three-dimensional (3D) model used for finite element (FE) simulation.
Figure 4B:
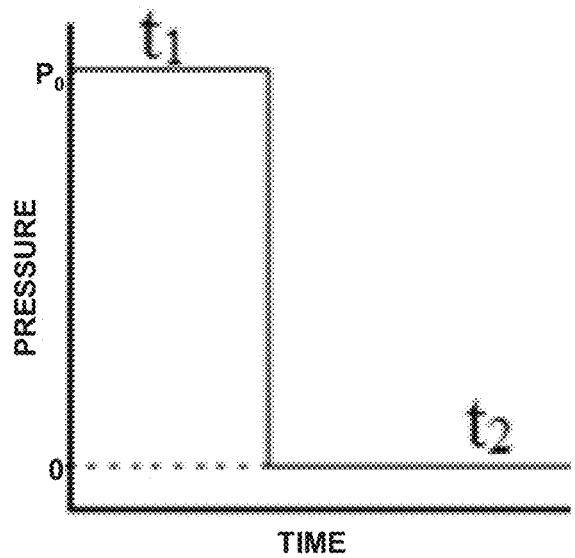
FIG. 4B shows a non-limiting example of a pulse input used for the FE simulation, where $t1=t2=10^{-4}$ s.
Figure 5A:
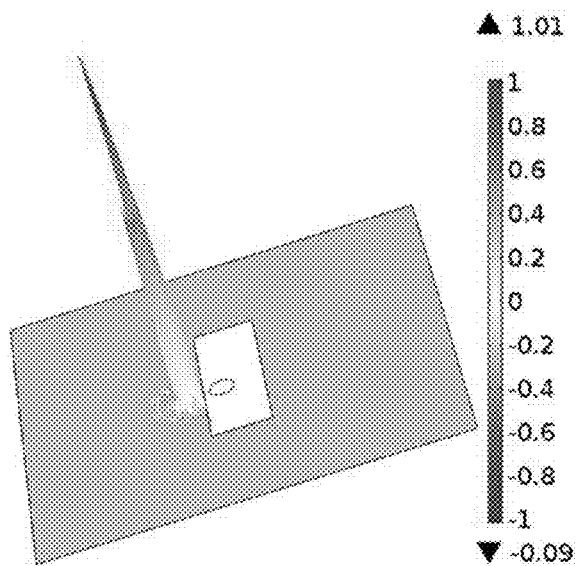
FIGS. 5A-5D show a pressure distribution of the 2D used for FE simulation.
Figure 5B:
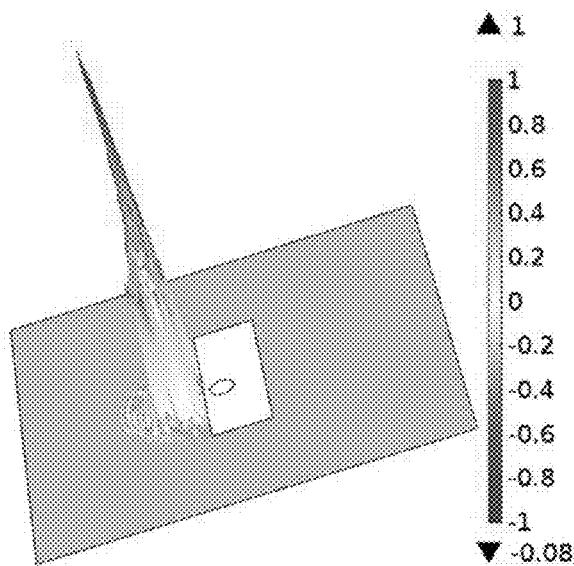
Figure 5C:
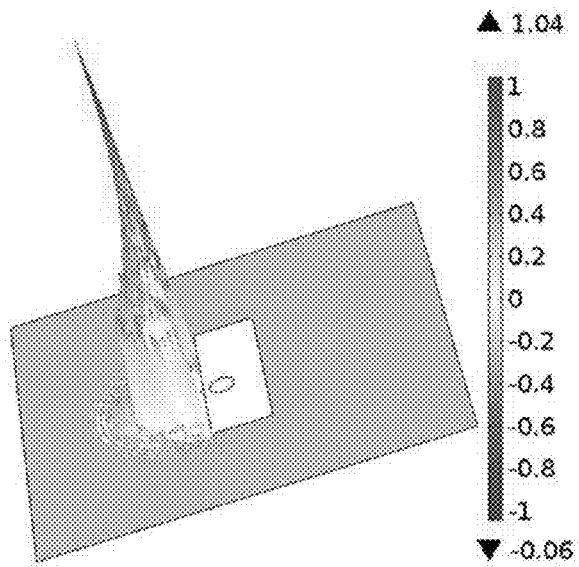
Figure 5D:
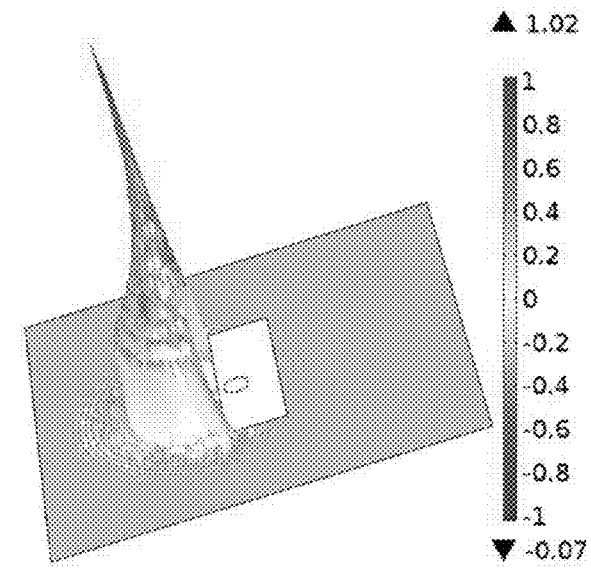

In order to establish the working of the FEA for the elastography system, instead of an actual CT scan, a 2D model is used. The 2D model shown in FIG. 4A includes an air domain (350×350 mm), a matrix (50×150 mm), and an inclusion (R10 mm). It may be appreciated that the tissue may be referred to as the matrix and organelles within the tissue may be referred to as the inclusion. As an example, the model may be considered for breast cancer (organelle) in breast tissues (matrix). As another example, aggregate (organelle) in concrete mortar (matrix) may be represented by the 2D model. Assumed properties are the elastic modulus of 1.5 kPa and the density of 1050 kg/m3 for the matrix, and the elastic modulus of 15 kPa and the density of 1050 kg/m3 for the inclusion. As such, the assumed properties are the first inputs that are used for optimization analysis and are typically obtained with reasonable guess. Matrix and inclusion are treated as linearly elastic and are assumed to have the same Poisson ratio of 0.49. A non-limiting example of an incident pulse wave is shown in FIG. 4B. The 3D simulation is modeled as the way expanding the 2D geometry in depth direction, 350×350×350 mm air domain, 50×50×150 mm matrix and spherical inclusion of 10 mm radius. Therefore, the 3D model has same cross-section across the center of the inclusion as the 2D model shown in FIG. 4A. Meanwhile, the 3D model has the same material properties and incident wave as those of the 2D model.

Figure 6A:
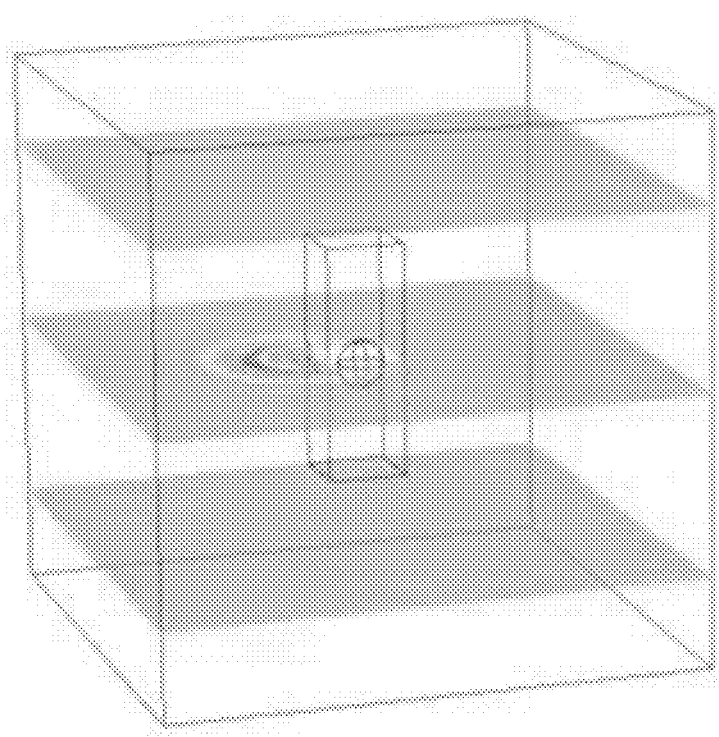
FIGS. 6A-6B show pressure distributions of the 3D model used for FE simulation.
Figure 6B:
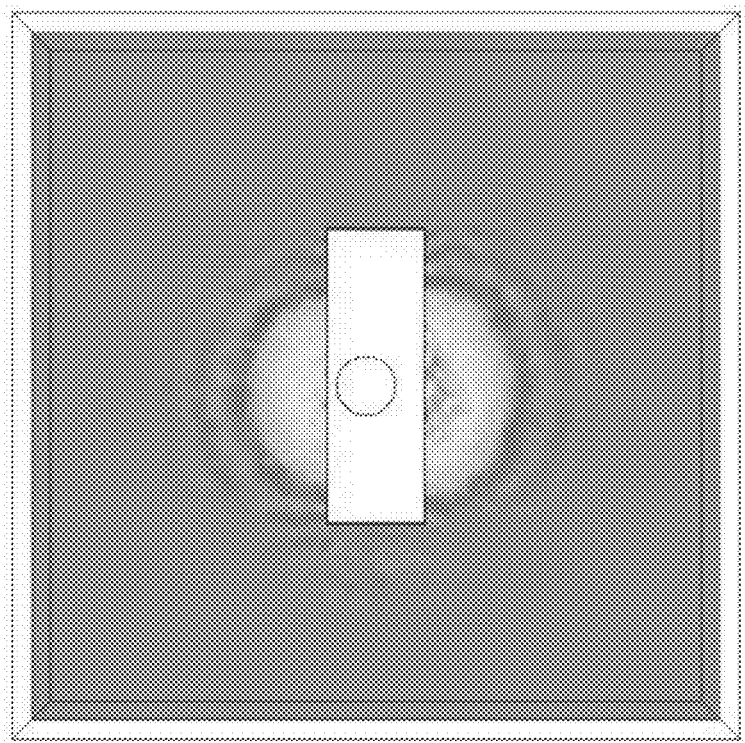

In both the 2D and the 3D numerical cases, the optimizing variables are the moduli of matrix and inclusion. In some embodiments, full factorial experiments may be employed to do the optimization instead of finding explicit solutions between the transmitted pressure and elastic moduli of samples. At this point, levels for each factor (variable) should be set firstly for using full factorial experiments method. In the two cases, 5 levels for each factor are designed: [0.8 1.2 1.6 2.0 2.5] kPa for the elastic modulus of matrix and [10 13 15 22 25] kPa for the modulus of inclusion. According to the principle of full factorial design, each case of 2D and 3D has 25 tries (25 times simulation). The typical pressure distribution of the 2D model is shown in FIG. 5, and that of the 3D model is shown in FIG. 6.

According to all of simulation and range analysis, the optimal value of the elastic modulus of the matrix for both 2D and 3D, 15 kPa, can be directly optimized out. The optimal value of the inclusion can be identified by parametric analysis. As such, the parametric analysis includes examining the behavior of the outputs as one or more of the inputs (or parameters) are systematically varied.

It can be concluded from these two numerical cases that the modulus can be identified in light of transmitted waves. At this point, the integration method has been initially validated with FE simulation.

In some embodiments, the wavelet synchro-squeezed transform (WSST) may be used on the output of FE method to estimate a mechanical property such as modulus of the matrix and the inclusion. The WSST may be used to decode pure shear or pure pressure waves and calculating the mechanical property based on the time reversal theory, as explained below.

Wavelet Synchro-Squeezed Transform (WSST) Method

The procedure using the wavelet synchro-squeezed transform (WSST) starts from the continuous wavelet transform (CWT), $$X_f(a,b) = \frac{1}{\sqrt{|a|}} \int_{-\infty}^{\infty} x(t)\bar{\varphi}\left(\frac{t-b}{a}\right)dt \quad (1)$$

where x(t) is the original signal, φ the complex conjugate of the mother wavelet, a the scale variable, and b the shifted variable. The next is to extract the instantaneous frequencies, $\omega_f(a,b)$, from $X_f(a,b)$, $$\omega_f(a,b) = -\frac{i}{X_f(a,b)} \frac{\partial X_f(a,b)}{\partial b} \quad (2)$$

Then WSST is the following, $$T_f(\omega_l, b) = \frac{1}{\Delta\omega} \sum_{a_k:|\omega_f(a_k,b)-\omega_l|\le\Delta\omega/2} X_f(a_k,b)a_k^{-\frac{3}{2}}(\Delta a)_k \quad (3)$$

where $\omega_l$ is the central frequency.

Accordingly, the original signal can be reconstructed as follows, $$x(t) = \text{Re}\left[C_\varphi^{-1} \sum_l T_f(\omega_l, b)\Delta\omega\right] \quad (4)$$

where $$C_\varphi = \frac{1}{2}\int_0^\infty \hat{\varphi}(\varepsilon)\frac{d\varepsilon}{\varepsilon},$$

with $\hat{\varphi}(\varepsilon)$ being the Fourier transform of the mother wavelet.

The mother wavelet is commonly the Morlet wavelet, $$\varphi(t) = \sqrt{\frac{2}{\pi f_l}}\left(e^{i2\pi f_l t} - e^{-\frac{1}{2}(2\pi f_l)^2}\right)e^{-\frac{1}{2}t^2} \quad (5)$$

WSST is used to decode what signals are the shear field and what are the pressure field. After that, the time reversal field will step in as follows, $$D^{TR}(r,t) = d(r_0,-t) \otimes d(r,t) = \Sigma_\tau d(r_0,\tau)d(r,t+\tau), \quad (6)$$

$$\epsilon^{TR}(t,t) = \epsilon(r_0,-t) \otimes \epsilon(r,t) = \Sigma_\tau \epsilon(r_0,\tau)\epsilon(r,t+\tau), \quad (7)$$

where ⊗ is the convolution operator, $D^{TR}(r,t)$ the time reversal displacement field, d(r,t) the measured displacement field, d(r_0,-t) the time-reversed displacement field of a virtual point sources at $r_0$, $\epsilon^{TR}(r,t)$ the time reversal strain field, ε(r,t) the measured strain field, ε($r_0$,−t) the time-reversed strain field of a virtual point sources at $r_0$. With these time reversal fields, if they are the pure shear or pressure wave induced deformation, the wavelength, $\lambda(r_0)$, is:

$$\lambda(r_0) \approx \frac{D^{TR}(r_0, 0)}{\epsilon^{TR}(r_0, 0)}. \qquad (8)$$

The wave velocity and the elastic modulus can be figured out in terms of $\lambda(r_0)$. Thus, a new method of characterizing the material's mechanical properties has been provided.

Figure 7:
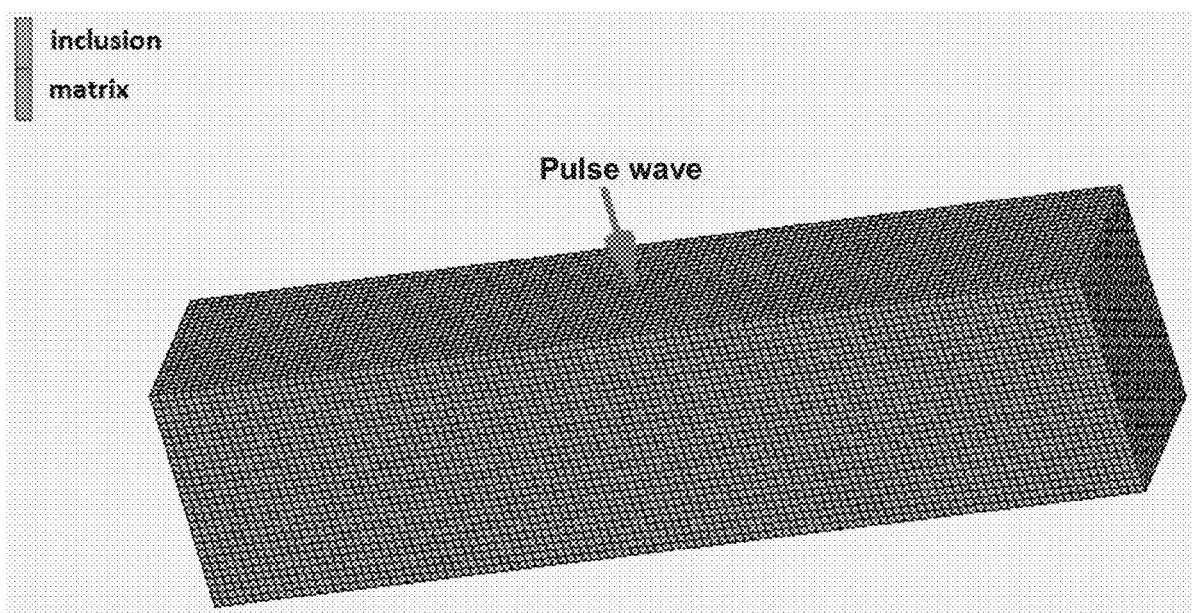
FIG. 7 shows a numerical composite material model.

In order to verify the method, as shown in FIG. 7 (406 mm×76 mm×102 mm), a 3D composite model is built in which the volume fraction of the matrix is 60% and that of the inclusion is 40%. The elastic modulus, Poisson ratio, and the density are 14 GPa, 0.17 and 2197.5 kg/m³, respectively, for the matrix and 45 GPa, 0.17 and 2688.9 kg/m³ for the inclusion.

Figure 8:
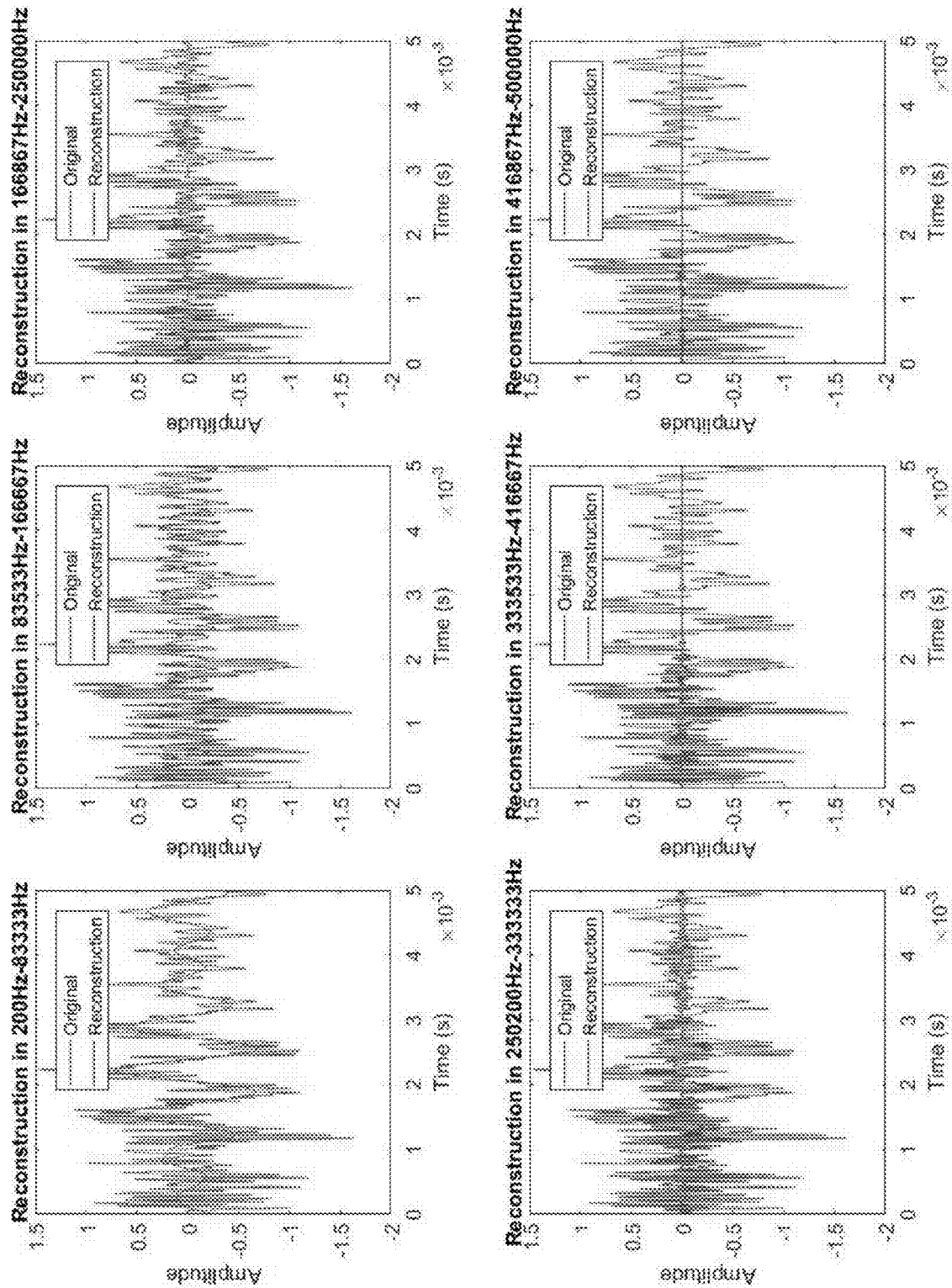
FIG. 8 shows a wavelet synchro-squeezed transform (WSST) signal processing.

During numerical simulation, a pulse wave in FIG. 4 is applied at the middle of the surface. Then the induced displacement and strain fields can be obtained. Two points near the two ends are picked for analysis. FIG. 8 shows a typical signal process using WSST, in which the reconstruction of WSST processing on the top left corner shows apparent shear signal that will be used to calculate the modulus based on equation (6) through equation (8). Finally, the elastic modulus is 16.0 GPa at one end and 20.9 GPa at another end, which illustrates the effect of composite heterogeneity. The new method applies to any frequency range. In this way, the mechanical properties of the tissue may be estimated using the WSST model using the transmitted signals and without using complex image processing. Thus, method 1700 requires transmitted signals to generate the mechanical property of the object either using FE model or using WSST model. It may be appreciated that no data is needed from inside of the object, resulting in an easier to implement method which is unaffected by noise in the imaging system. In addition, the method is more efficient because the analysis of the mechanical properties is performed without using any sophisticated image processing.

While it has been described a forward analysis using FE methods, and an inverse analysis using WSST and time reversal theory, it is to be understood that the present invention in not limited to the use of these specific methods and techniques. In some embodiments, the present invention may utilize any suitable and appropriate forward analysis methods and inverse analysis methods known to one of ordinary skill in the art.

Experimental Validation

The present invention has been validated both in numerical simulation stage and experimental stage.

Figure 9A:
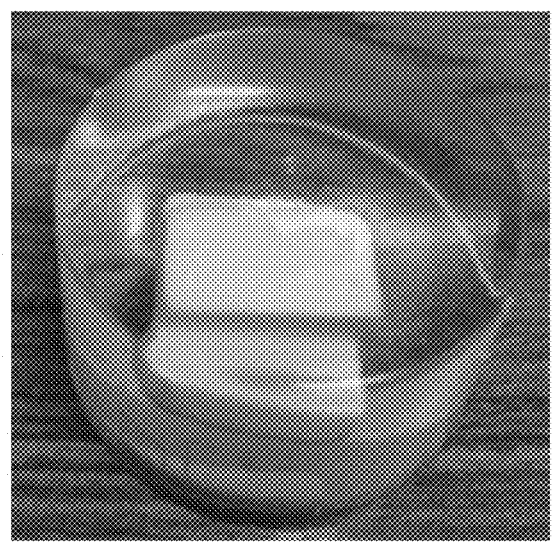
FIG. 9A shows a picture of a sample made of silicone matrix having an eraser inclusion.
Figure 9B:
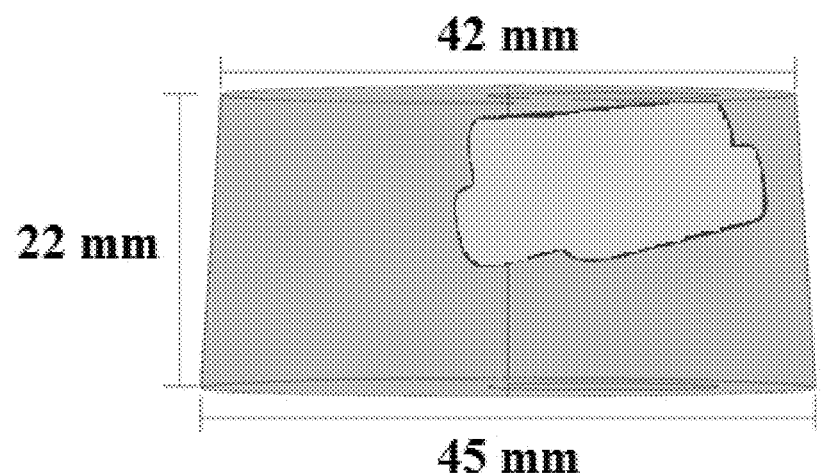
FIG. 9B shows a cross-section of the sample of FIG. 9A.
Figure 10:
FIG. 10 shows a 3D image of the inclusion.
Figure 11:
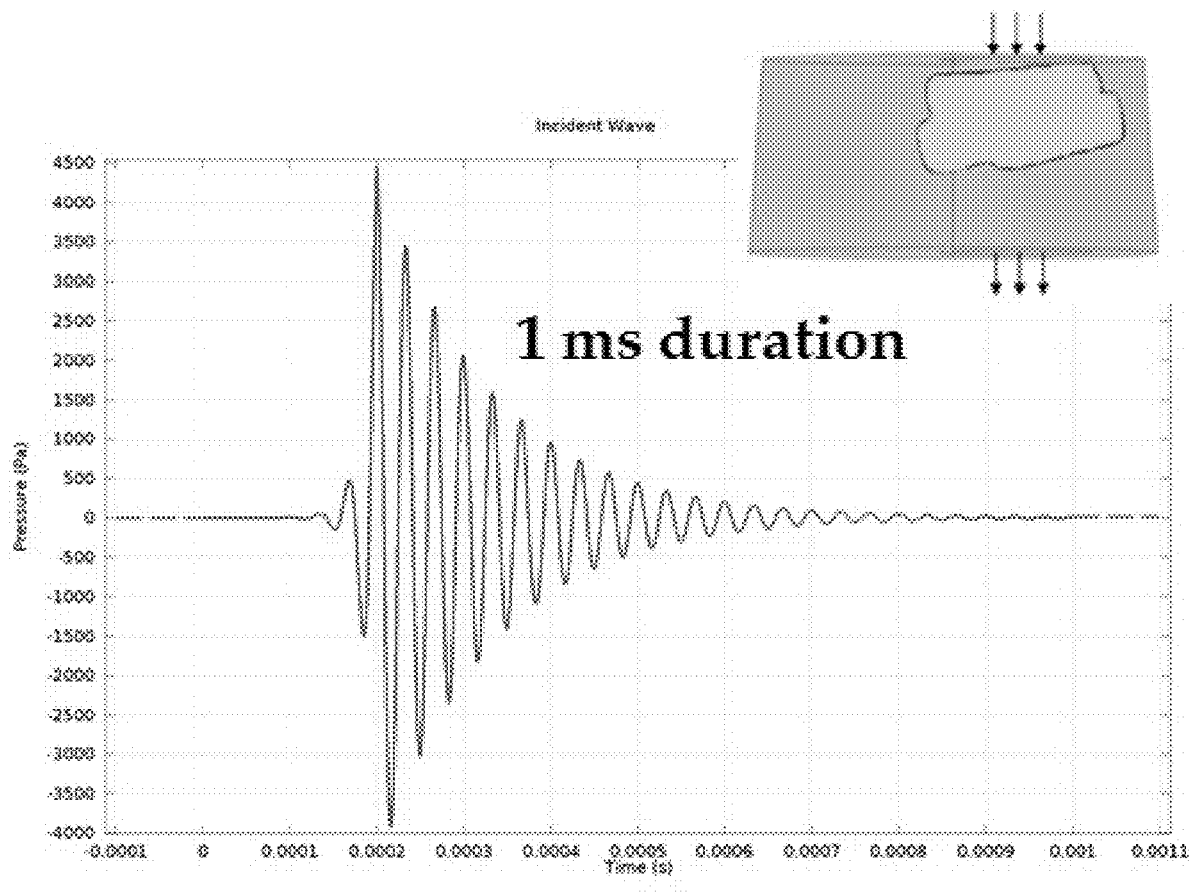
FIG. 11 shows a profile of an incident wave transmitting through the sample.
Figure 12:
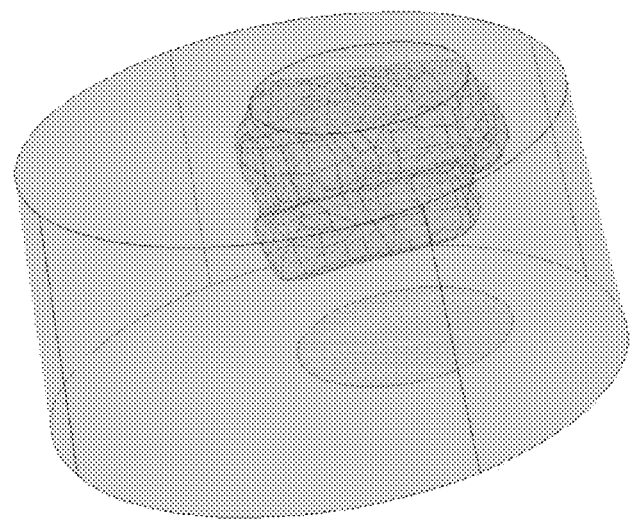
FIG. 12 shows a FE simulating model.

Sample: The sample is made of the silicone rubber as the matrix and the eraser material as the inclusion as shown in FIG. 9. The first step is to scan the sample to get the internal structure of the sample. FIG. 10 shows the inclusion geometry scanned by Nano CT. The second step to have sound test on the same sample and acquire the transmitted signals. The incident wave in current experiments is a 30 kHz sine tone burst of 4467 Pa peak value as shown in FIG. 11. The output peak is 22.4 Pa that will be optimization objective. The pulser and receiver have the same aperture, 17 mm. The third step includes FE modeling wherein the inclusion geometry resolved by Nano CT scan is imported into COMSOL, which is a commercial FE software as shown in FIG. 12 in which matrix geometry is built by COMSOL. One smaller circle on the top of the sample demonstrates the loading area of the incident wave, another one below on the bottom demonstrates the transmitted signal acquisition area where the receiver is placed. The two circles have the diameter of 17 mm same as the aperture of sound transducers. The fourth step includes performing inverse analysis. In this experimental case, 6 factors (optimizing variables) are chosen: moduli, Poisson ratio and density of matrix and inclusion, 5 levels are set for each factor as presented in Table 1. Because there are more factors, the orthogonal array design is employed to conduct the inverse analysis. The array of six 5-level factors is totally 25 times simulation according to the principle of orthogonal design.

TABLE 1

Levels for each factor is shown below.

| Material | Factors | Levels | | | | |
|---|---|---|---|---|---|---|
| Matrix | Modulus (MPa) | 1.2 | 1.6 | 2.0 | 2.4 | 2.8 |
| | Poisson Ratio | 0.30 | 0.35 | 0.40 | 0.45 | 0.49 |
| | Density (kg/m³) | 1000 | 1050 | 1100 | 1150 | 1200 |
| Inclusion | Modulus (MPa) | 2.2 | 2.6 | 3.0 | 3.4 | 3.8 |
| | Poisson Ratio | 0.35 | 0.39 | 0.43 | 0.47 | 0.49 |
| | Density (kg/m³) | 1500 | 1600 | 1700 | 1800 | 1900 |

In order to reduce computational time, the transmission of sound at the interface between transducers and sample is considered in advance, which means the acoustic-structural coupled analysis will become the structural transient analysis. Another reason doing the transition is that only transmitted data, not the propagation in the air, is useful. At this point, the transmission coefficient should be updated at each try in orthogonal array during FE simulating. The wave transmitted into sample is the incident wave multiplied by the transmission coefficient.

Figure 13:
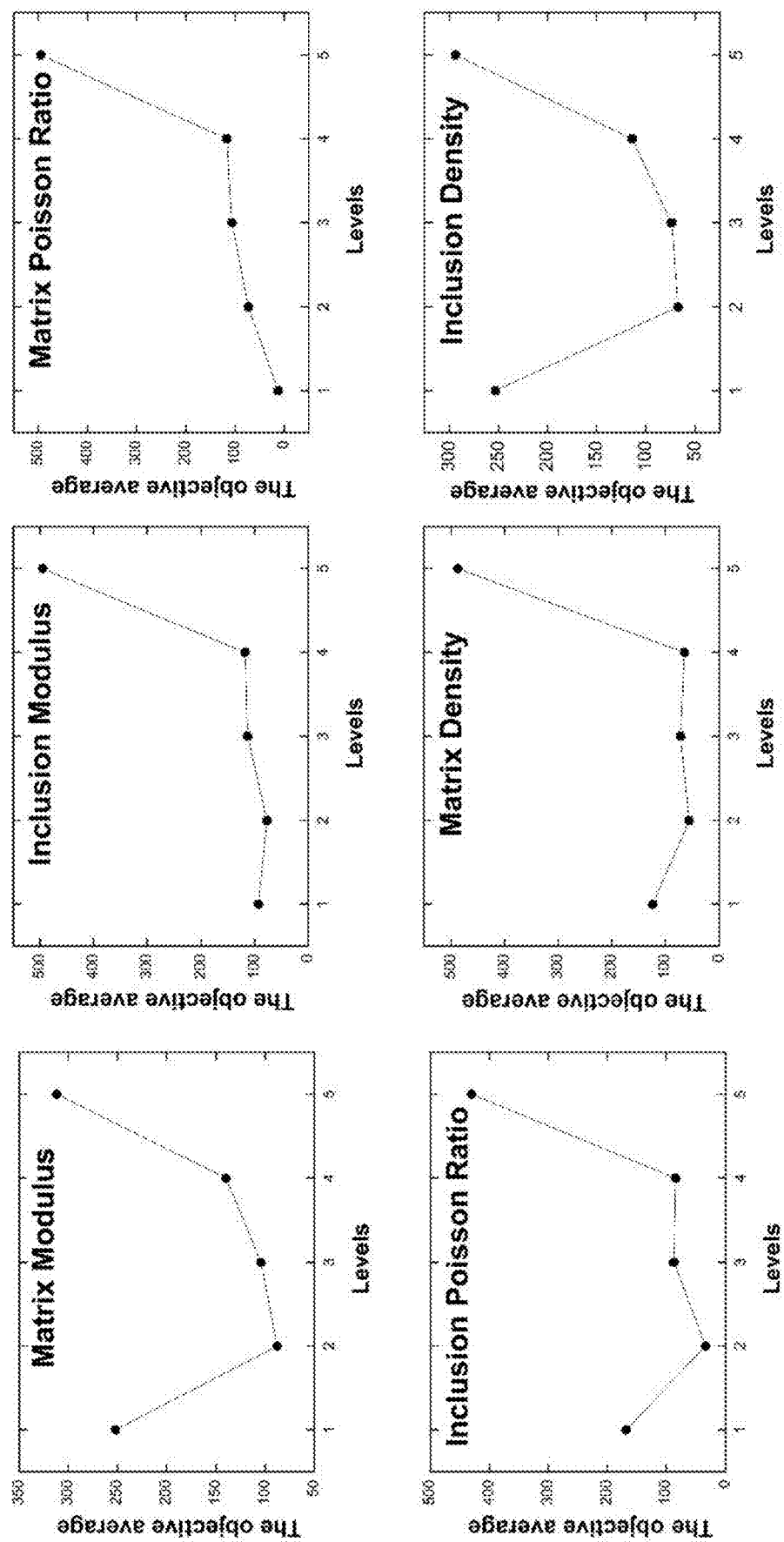
FIG. 13 shows plots of objective average of each level and a level factor for each factor.
Figure 14:
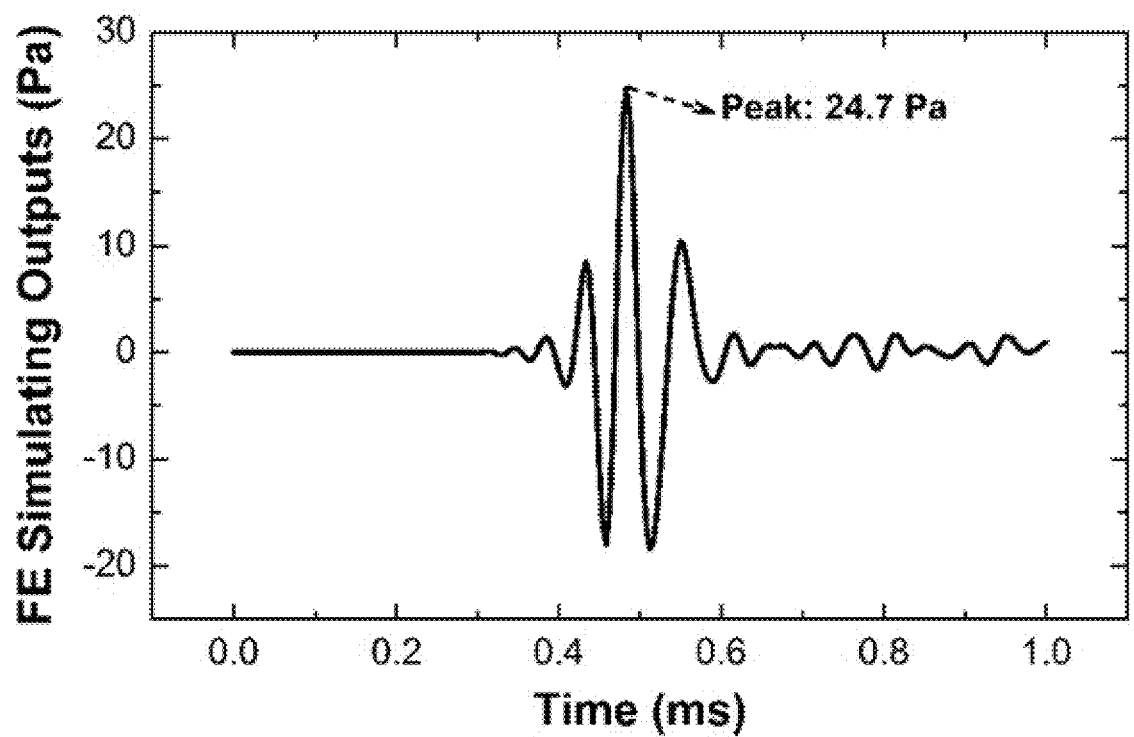
FIG. 14 shows FE pressure output of optimum values.

Taking the 22.4 Pa detected by the sound receiver as the optimizing object, after completing all simulation listed in orthogonal array and according to range analysis, optimum values can be read out directly from FIG. 13 in which x-coordinate is the level number for each factor, and the vertical is the objective average of a level. The lowest point in FIG. 13 is the optimum value for each factor: modulus of 1.6 MPa, Poisson ration of 0.30 and density of 1050~1150 kg/m3 for matrix, and 2.6 MPa, 0.39 and 1600~1700 kg/m3 for inclusion. FIG. 14 shows the FE pressure output of the set of optimum values (1.5 MPa, 0.3 and 1050 kg/m3 for matrix, and 2.6 MPa, 0.39 and 1600 kg/m3 for inclusion), which illustrates that the FE peak value, 24.7 Pa, matches with the objective, 22.4 Pa.

Figure 15:
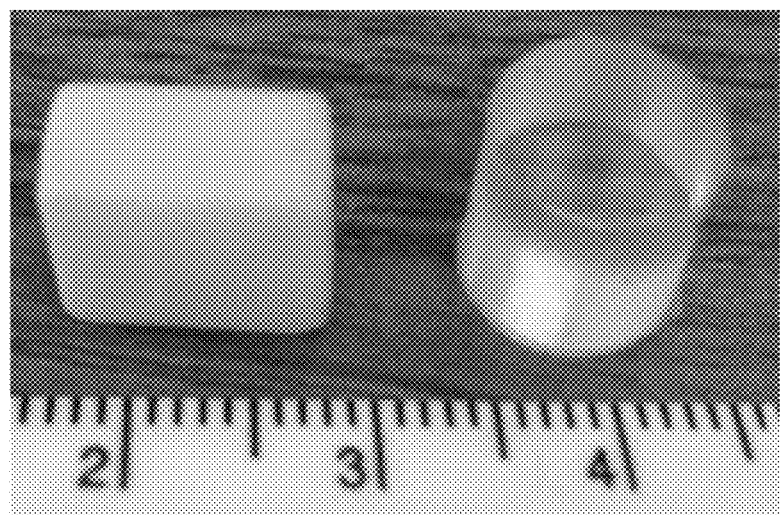
FIG. 15 shows pictures of the samples used for compression tests.
Figure 16A:
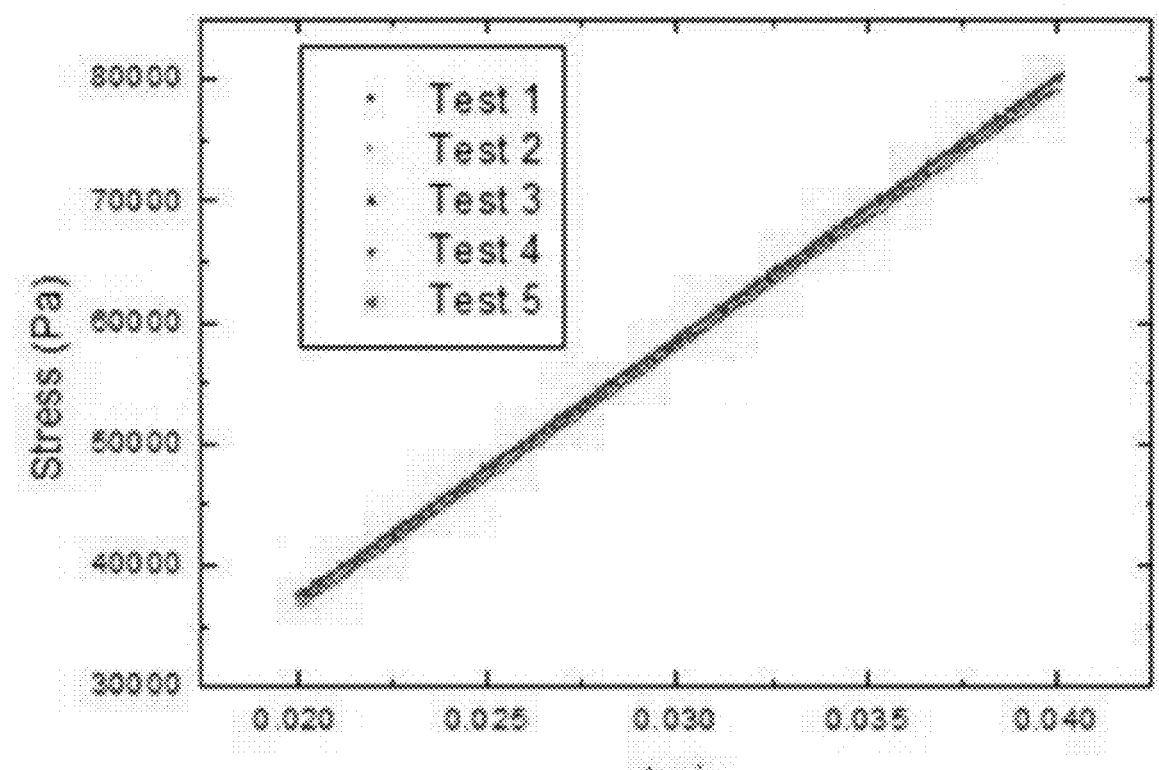
FIGS. 16A-16B shows results of the compression tests of the silicone matrix and the eraser inclusion.
Figure 16B:
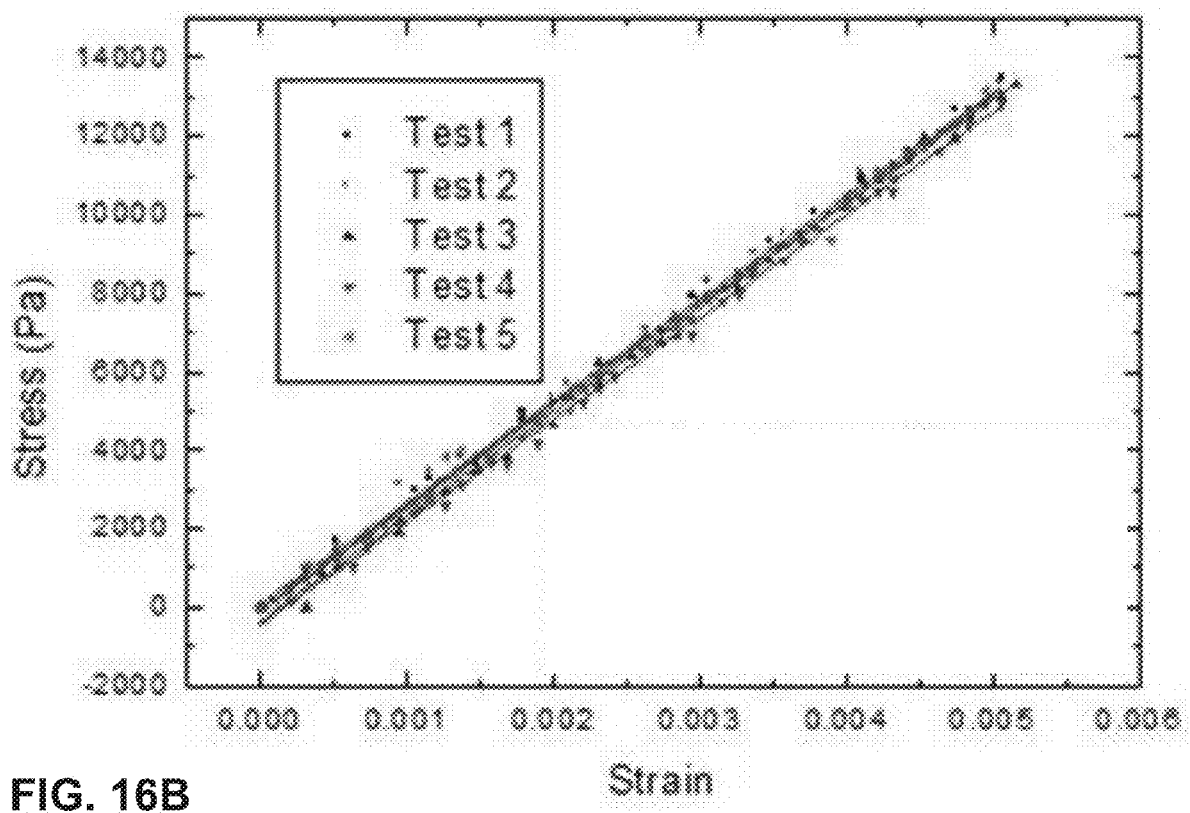

The final step includes verification of optimum values. The material properties of matrix and inclusion has been optimized out. Verification is necessary to see if the optimization is real. Some measurements are done for measuring the density and moduli of matrix and inclusion. The measured density is 1050 kg/m3 for matrix, 1690 kg/m3 for inclusion. The modulus is measured by uniaxial compression test. The samples are shown in FIG. 15. The compression speed is 0.01 mm/s until the strain is up to 10%. Five tests are conducted for each sample, and then follows by linear fit on stress-strain curves as shown in FIG. 16. The slopes of these fits is the modulus: 2.1 MPa for matrix and 2.6 MPa for inclusion. It can be concluded that the optimization agrees well with the measured values. Thus, the present invention has been validated by FE simulation and experiments.

SIMULATION EXAMPLE 2

The following is another non-limiting example of a numerical simulation on real multiphase soft tissues. It is to be understood that the example described herein is presented for illustrative purposes, and is not intended to limit the invention in any way. Equivalents or substitutes are within the scope of the invention.

Figure 17:
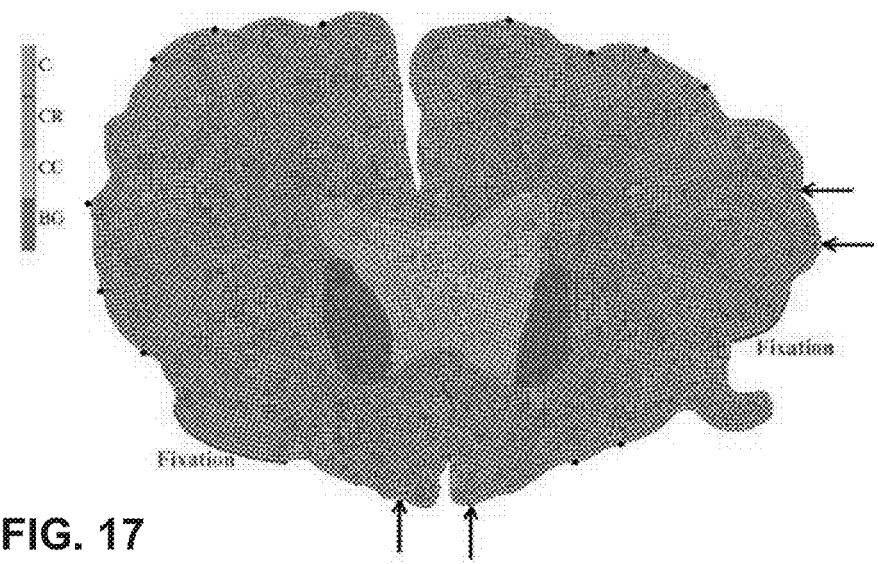
FIG. 17 shows a brain-tissue slice segmented into four regions meshed for FEM simulation, including the cortex (C), corona radiata (CR), corpus callosum (CC) and basal ganglia (BG). The four arrows show the incidence positions and the 12 black solid dots show the signal detection locations. The 'Fixation' boundaries marked by red curves mean that displacement is constrained to be zero during FEM simulation.
Figure 18A:
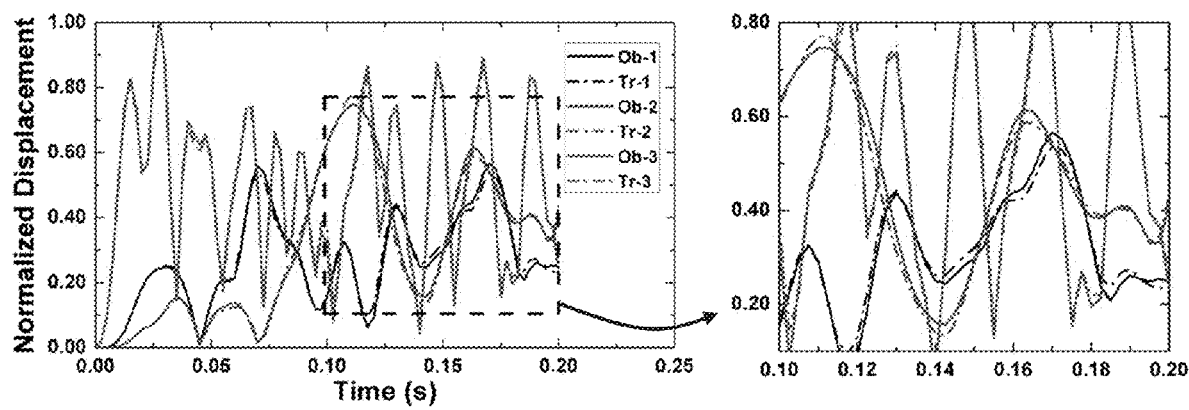
FIGS. 18A-18B show a comparison of the target signals and the best trial signals in the first round and the fourth round, respectively. 'Ob' stands for the target signals and 'Tr' for the output ones from the best trial.
Figure 18B:
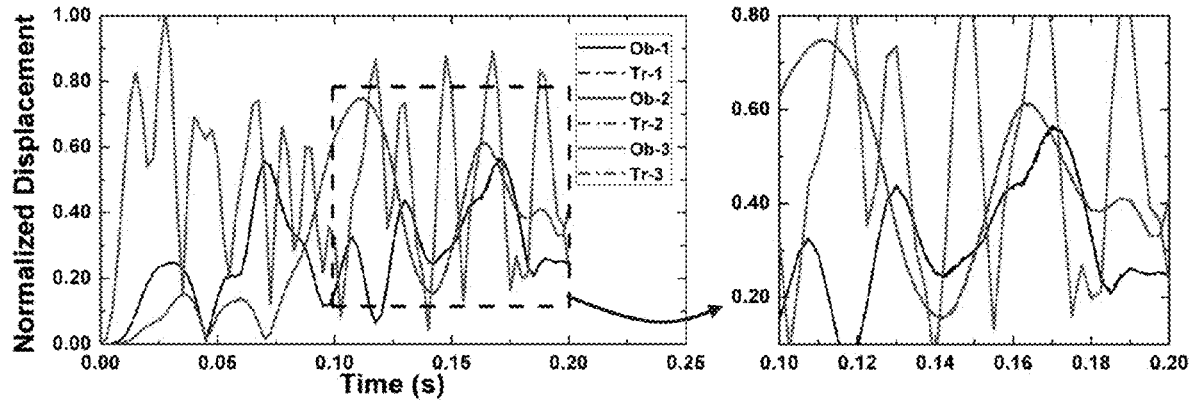

Numerical model creation and simulation were conducted on the commercial FEM package, *Marc Mentat* 2018.0.0 (64 bit) (MSC Software Corporation), with the assist of a Python script performing the factorial design, the parameter update and mathematical process. A brain slice was segmented into four regions and simulated as shown in FIG. 17. The model was meshed into 11261 four-node quadrilateral elements. The incident wave is the 50 Hz sine signal applied at four positions on the outer boundary denoted by arrows. As denoted by the black sold dots, twelve locations were chosen to detect the transmission with the sample rate of 400/s. The acquisition duration is 0.2 s. All tissues were treated as linear elasticity for demonstrating the integrated method first on linear materials. The set of shear moduli, [C=1.43, CR=0.66, CC=0.35, BG=0.70] kPa, was used as the objective values and the corresponding output at 12 locations as the objective signals. Accordingly, the eleastic moduli are [4.26, 1.97, 1.04, 2.09] kPa if Poisson's ratio of 0.49 is assumed for all tissues. The density is assumed 1000 kg/m³. In this case, full factorial design was employed to recognize the optimality for all levels of factors. Hence, there are four factors corresponding to elastic moduli of C, CR, CC and BG.

In terms of the reseasonable ranges of their moduli, 3.0 kPa~6.0 kPa for region C and 0.1 kPa~3.0 kPa for other three regions, each factor is assigned eight levels at first, [3.0, 3.4, 3.8, 4.2, 4.6, 5.0, 5.4, 6.0] kPa for C and [0.1, 0.5, 0.9, 1.3, 1.7, 2.1, 2.5, 3.0] for others. Totally, it is $8^4$ (4096) trials for possible combinations of all levels. Running on a PC with Intel® Core™ i7-3770 CPU @ 3.40 GHz and 16.0 GB RAM, each trial takes 21 seconds. Because cross-correlation can be used to observe the similarity of two signals, the objective function is established based on the cross-correlation of the objective signals and each trial ones. The maximum of cross-correlation is at the zero lag time if two signals are identical, which is called auto-correlation. For this case, the objective function of the optimizatioin problem is defined as:

$$\min f(E) = \sqrt{\sum_{i=1}^{12}\left(1 - \frac{D_C^i|_{t=0}}{D_A^i|_{t=0}}\right)^2} \quad (9)$$

Subject to: $\min f(E) \le 1.0\%$ where $E=(E_C, E_{CR}, E_{CC}, E_{BG})$, standing for the elastic moduli attempt in each level, $D_A^i|_{t=0}$ is the auto-correlation of the measured signals of point i at the zero lag time, and $D_C^i|_{t=0}$ is the cross-correlation of the trial signals and the measured signals of point i at the zero lag time. The effect of E on $D_C^i|_{t=0}$ is implicit in equation (9). But, they are bridged in FEM in which E are the material parameter input and $D_C^i|_{t=0}$ is determined according to FEM output. The measured signals that are the objective signals come from the FEM simulation with the objective elastic moduli of [4.26, 1.97, 1.04, 2.09] kPa. Applying equation (9) to 4096 trials, min f (E) is reached at [4.2, 2.1, 0.9, 2.1] kPa of the $2732^{nd}$ trial, meaning that the $2732^{nd}$ one is the closest to real values among all trials. The error of the trial is 4.3%, larger than 1.0%, which can be sufficient for mapping elasticity. As an illustration for three surface locations, the objective signals of the displacement amplitude and the corresponding simulation signals of the best trial 2732 are plotted in FIG. 18A. In contrast, there is discrepancy for some locations between two sets of signals, which causes the 4.3% error.

To present a more accurate solution, the inverse analysis is continued until a min f(E)≤1.0% is achieved. The first round helps to compress the value ranges for the later rounds. As a result, based on each value in [4.2, 2.1, 0.9, 2.1] kPa of the first-round, the next round factorial design with the smaller step sets [3.90, 4.05, 4.20, 4.35, 4.50] for C, [1.80, 1.95, 2.10, 2.25, 2.40] for CR, [0.60, 0.75, 0.90, 1.05, 1.20] for CC and [1.80, 1.95, 2.10, 2.25, 2.40] for BG, which introduces 625 trials. This round ends up with [4.20, 2.10, 1.05, 2.10]. Because the result is almost the same as that of the first-round, the step of levels is needed to be further decreased. Levels of the third round are set to [4.10, 4.15, 4.20, 4.25, 4.30] for C, [2.00, 2.05, 2.10, 2.15, 2.20] for CR, [0.80, 0.85, 0.90, 0.95, 1.00] for CC and [1.85, 1.90, 1.95, 2.00, 2.05] for BG. After all trials are completed, the third round gives [4.25, 2.00, 1.00, 2.05] with 4.1%. Once more, the level range of the fourth round is narrowed down with the much smaller step, [4.23, 4.25, 4.27] for C, [1.98, 2.00, 2.02] for CR, [0.98, 1.00, 1.02] for CC and [2.03, 2.05, 2.07] for BG. Eventually, [4.27, 1.98, 1.02, 2.07] is finalized as the optimum trial with 1.0%. The comparison of the objective signals and the corresponding ones of the best trial is plotted in FIG. 18B for the same locations as in FIG. 18A. The two set of signals are almost overlapping, which illustrates again [4.27, 1.98, 1.02, 2.07] are the optimum values, consistent with real elastic moduli of [4.26, 1.97, 1.04, 2.09] with errors 0.2%, 0.5%, 1.9% and 1.0%, respectively.

During the entire course, any internal information is neither detected nor processed to map the moduli. Instead, the present invention demonstrates that all information for the mapping can be based on signals on the 12 surface locations. Without wishing to limit the present invention to a particular theory or mechanism, the mechanical response of the sample can be determined without relying on response acquisitions or other invasive procedures within the sample, as the mechanical properties of the inclusion can be deduced from analysis performed on parameters of the surface of the sample.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An integrated elastography system (100) for estimating mechanical properties of a sample (110), the system comprising:
   a) an x-ray computed tomography ("CT") system (101) comprising an x-ray source (102) and a detector (108), wherein the x-ray source emits x-rays towards the sample (110) and wherein the detector (108) collects x-rays emitted from the sample (110);
   b) a sound wave system (103) having one or more acoustic transducers (112) and one or more receivers (114) configured to be positioned around an outer surface of the sample (110), wherein the one or more transducers (112) are configured to generate sound waves that impinge on the sample (110), and wherein the one or more receivers (114) receive a first set of transmitted signals comprising sound waves that transmit through the sample (110); and
   c) a controller (120) operably coupled to the x-ray CT system (101) and the sound wave system (103), wherein the controller (120) has a memory that stores computer readable instructions that, when executed by the controller, causes the controller to:
      i) generate only one x-ray CT image of the sample using the detected x-rays from the sample, and select a matrix and an inclusion based on geometries detected from the CT image of the sample;
      ii) generate the first set of transmitted signals based on the CT image using the sound wave system (103);
      iii) select an initial set of values comprising one or more of an elasticity modulus, a Poisson ratio, and a density for the matrix and the inclusion based on the selection; and
      iv) perform and repeat a forward analysis sequence to simulate a sound wave transmission through the matrix and the inclusion to deduce a mechanical response of the matrix and the inclusion, wherein the forward analysis sequence optimizes the initial set of values until the set of signals generated converges with the first set of transmitted signals;
   wherein the mechanical response is determined based on the set of signals generated, thereby decoding the mechanical response of the sample without requiring response acquisitions from inside the sample.

2. The system of claim 1, wherein the forward analysis sequence comprises constructing a finite element ("FE") model by generating a mesh of each of the matrix and of the inclusion from the CT image, wherein the mesh is generated using an approximation of the geometries of the matrix and the inclusion, and wherein generation of the mesh includes dividing the CT image into smaller finite elements.

3. The system of claim 1, wherein the memory includes additional instructions that, when executed by the controller, cause the controller to perform an inverse analysis on the set of signals to deduce a modulus of each of the matrix and the inclusion.

4. The system of claim 3, wherein the inverse analysis comprises a wavelet synchro-squeezed transform ("WSST") comprising:
   a) generating a continuous wavelet transform from the set of signals;
   b) extracting instantaneous frequency from the continuous wavelet transform;
   c) reconstructing transmitted signals from continuous wavelet transform and the frequency;
   d) decoding the reconstructed transmitted signals into shear signals and pressure signals; and
   e) estimating the modulus of the sample based on one or more of the shear signals and the pressure signals, thereby decoding the mechanical property of the sample using the x-ray CT image and the transmitted signals, wherein the estimation is based on a time reversal theory, wherein the modulus is estimated from the shear signals and the pressure signals.

5. The system of claim 1, wherein the one or more transducers (112) are disposed on a surface of an enclosure of the integrated elastography system (100) and wherein the one or more receivers (114) are in contact with outer surface of the sample (110).

6. The system of claim 1, wherein the sound waves comprise a sine tone burst.

7. The system of claim 1, wherein the initial set of values is selected based on an estimate of the elasticity modulus, the Poisson ratio, and the density for the matrix and the inclusion.

8. The system of claim 1, wherein the mechanical response includes one or more of displacement, velocity, acceleration, and a pressure within the sample.

9. The system of claim 1, wherein the sample is a biological sample, wherein the matrix comprises tissue and the inclusion comprise non-tissue biological material.

10. The integrated elastography system of claim 9, wherein the biological material is a tumor or foreign mass.

11. The integrated elastography system of claim 1, wherein the sample is a composite material comprising particles embedded in a solid medium.

12. An integrated elastography system (100) comprising:
   a) an x-ray computed tomography ("CT") system (101) comprising an x-ray source (102) and a detector (108), wherein the x-ray source emits x-rays towards a sample (110) and wherein the detector (108) collects x-rays emitted from the sample (110);
   b) a sound wave system (103) having a plurality of acoustic transducers (112) and a plurality of receivers (114) configured to be positioned at or near an outer surface of the sample (110), wherein the plurality of transducers (112) are configured to generate sound waves that impinge on the sample (110), and wherein the plurality of the receivers (114) receive a first set of transmitted signals, wherein the first set of transmitted signals include the sound waves that transmit through the sample (110); and
   c) a controller (120) operably coupled to the x-ray CT system (101) and the sound wave system (103), wherein the controller (120) has memory that stores computer readable instructions that, when executed by the controller, causes the controller to:
      i. generate only one x-ray CT image of the sample using the detected x-rays from the sample, and select a matrix and an inclusion based on geometries detected from the CT image of the sample;

ii. generate a mesh of each of the matrix and of the inclusion from the CT image, wherein the mesh is generated using an approximation of the geometries of the matrix and the inclusion, and wherein generation of the mesh includes dividing the CT image into smaller finite elements;

iii. choose an initial set of values comprising one or more of an elasticity modulus, a Poisson ratio, and a density for the matrix and the inclusion based on the selection;

iv. perform a finite element analysis on the CT image using the set of initial values of an elasticity modulus, a Poisson ratio, and a density of the sample to generate a second set of signals;

v. perform a wavelet synchro-squeezed transform ("WSST") on a deformation of shear and pressure waves outputted from the finite element analysis to generate a continuous wavelet transform;

vi. extract an instantaneous frequency from the continuous wavelet transform;

vii. reconstruct the transmitted signals from the continuous wavelet transform and the frequency;

viii. decode the reconstructed transmitted signals into shear signals and pressure signals;

ix. repeat step (iv)-(viii) to optimize the set of initial values and generate subsequent set of signals until the set of signals converge with the first set of transmitted signals; and x. estimate an elastic modulus of the sample based on one or more of the shear signals and the pressure signals, wherein the estimation is based on a time reversal theory, and wherein a mechanical property of the sample is estimated from the elastic modulus, thereby decoding the mechanical property of the sample using the x-ray CT image and the transmitted signals without relying on response acquisitions from inside the sample.

13. The integrated elastography system of claim 12, wherein the time reversal theory includes generating a time reversal displacement field and a time reversal strain field, wherein the elastic modulus is determined from a ratio of the time reversal displacement field and the time reversal strain field.

14. The integrated elastography system of claim 12, wherein the sound waves comprise a sine tone burst.

15. The integrated elastography system of claim 12, wherein the initial set of values are chosen based on an estimate of the elasticity modulus, the Poisson ratio, and the density for the matrix and the inclusion.

16. A method for determining a modulus of a sample, the method comprising:

(a) obtaining only one x-ray computed tomography ("CT") image of the sample using x-rays collected from the sample, wherein the x-rays are collected using an x-ray CT system (101) comprising an x-ray source (102) and a detector (108), wherein the x-ray source emits x-rays towards the sample (110) and the detector (108) collects x-rays emitted from the sample (110);

(b) positioning at or near an outer surface of the sample (110) a sound wave system (103) comprising one or more acoustic transducers (112) and one or more receivers (114), wherein the one or more transducers (112) generate sound waves that impinge on the sample (110), and the one or more receivers (114) receive a first set of transmitted signals;

(c) impinging the sample with sound waves generated from the one or more transducers (112), wherein the one or more receivers (114) receive the first set of transmitted signals comprising the sound waves that transmit through the sample (110);

(d) performing a finite element analysis on the CT image using a set of initial values of an elasticity modulus, a Poisson ratio, and a density of the sample to generate a second set of signals;

(e) performing a cycle operation of optimizing the set of initial values to generate subsequent sets of signals until the set of signals converges with the first set of transmitted signals; and (f) determining a mechanical response of the sample based on the optimized set of initial values, wherein the mechanical response includes one or more of a displacement, a velocity, an acceleration, and a pressure of the sample.

17. The method of claim 16, further comprising performing an inverse analysis on the set of signals generated to deduce a modulus of the sample.

18. The method of claim 17, wherein the inverse analysis comprises a wavelet synchro-squeezed transform ("WSST") comprising:

(a) generating a continuous wavelet transform from the set of signals;

(b) extracting instantaneous frequency from the continuous wavelet transform;

(c) reconstructing transmitted signals from continuous wavelet transform and the frequency;

(d) decoding the reconstructed transmitted signals into shear signals and pressure signals; and (e) estimate the elastic modulus of the sample based on one or more of the shear signals and the pressure signals, wherein the estimation is based on a time reversal theory, and wherein the elastic modulus is estimated from the shear signals and the pressure signals, thereby decoding mechanical property of the sample using the x-ray CT image and the transmitted signals.

19. The method of claim 16, wherein performing the finite element analysis on the CT image comprises:

(a) selecting a matrix and an inclusion based on geometries detected from the CT image of the sample; and (b) generating a mesh of each of the matrix and of the inclusion, wherein the mesh is generated using an approximation of the geometries of the matrix and the inclusion from the CT image, and wherein generation of the mesh includes dividing the CT image into smaller finite elements.

20. The method of claim 19, further comprising determining the mechanical response and the modulus of each of the matrix and the inclusion.

* * * * *